United States Patent [19]

Fidel et al.

[11] Patent Number: 4,601,292
[45] Date of Patent: Jul. 22, 1986

[54] STEERABLE DOPPLER TRANSDUCER PROBES

[75] Inventors: Howard F. Fidel, Hartsdale; David L. Greenwood, New York, both of N.Y.

[73] Assignee: Johnson & Johnson Ultrasound, Inc., Ramsey, N.J.

[21] Appl. No.: 669,703

[22] Filed: Nov. 8, 1984

[51] Int. Cl.⁴ .............................................. A61B 10/00
[52] U.S. Cl. ................................... 128/660; 128/661; 128/663; 73/625
[58] Field of Search ......................... 128/660, 661, 663; 73/618, 621, 633, 861.25, 625, 628, 641

[56] References Cited

U.S. PATENT DOCUMENTS

| 4,097,835 | 6/1978 | Green | 128/663 |
|---|---|---|---|
| 4,130,022 | 12/1978 | Goodrich et al. | 128/660 |
| 4,141,347 | 2/1979 | Green et al. | 128/663 |
| 4,373,533 | 2/1983 | Iinuma | 128/663 |
| 4,407,293 | 10/1983 | Suarez, Jr. et al. | 128/663 |
| 4,416,286 | 11/1983 | Iinuma et al. | 128/663 |
| 4,421,118 | 12/1983 | Dow et al. | 128/660 |
| 4,424,813 | 1/1984 | Havlice et al. | 128/660 |
| 4,492,120 | 1/1985 | Lewis et al. | 128/663 |

FOREIGN PATENT DOCUMENTS 2935497  3/1981  Fed. Rep. of Germany ........ 73/633

Primary Examiner—Kyle L. Howell
Assistant Examiner—Ruth S. Smith
Attorney, Agent, or Firm—W. Brinton Yorks, Jr.

[57] ABSTRACT

An ultrasonic diagnostic probe is provided which performs simultaneous ultrasonic imaging and Doppler flow measurement. The Doppler transducer is mounted for rotation by a mechanical assembly, which permits the Doppler beam to be steered during imaging to the point in the body where a flow measurement is to be taken. As the Doppler transducer is rotated, a variable impedance device within the probe is adjusted in correspondence with the transducer rotation so as to provide an indication signal of the direction in which the Doppler beam is being directed.

13 Claims, 8 Drawing Figures

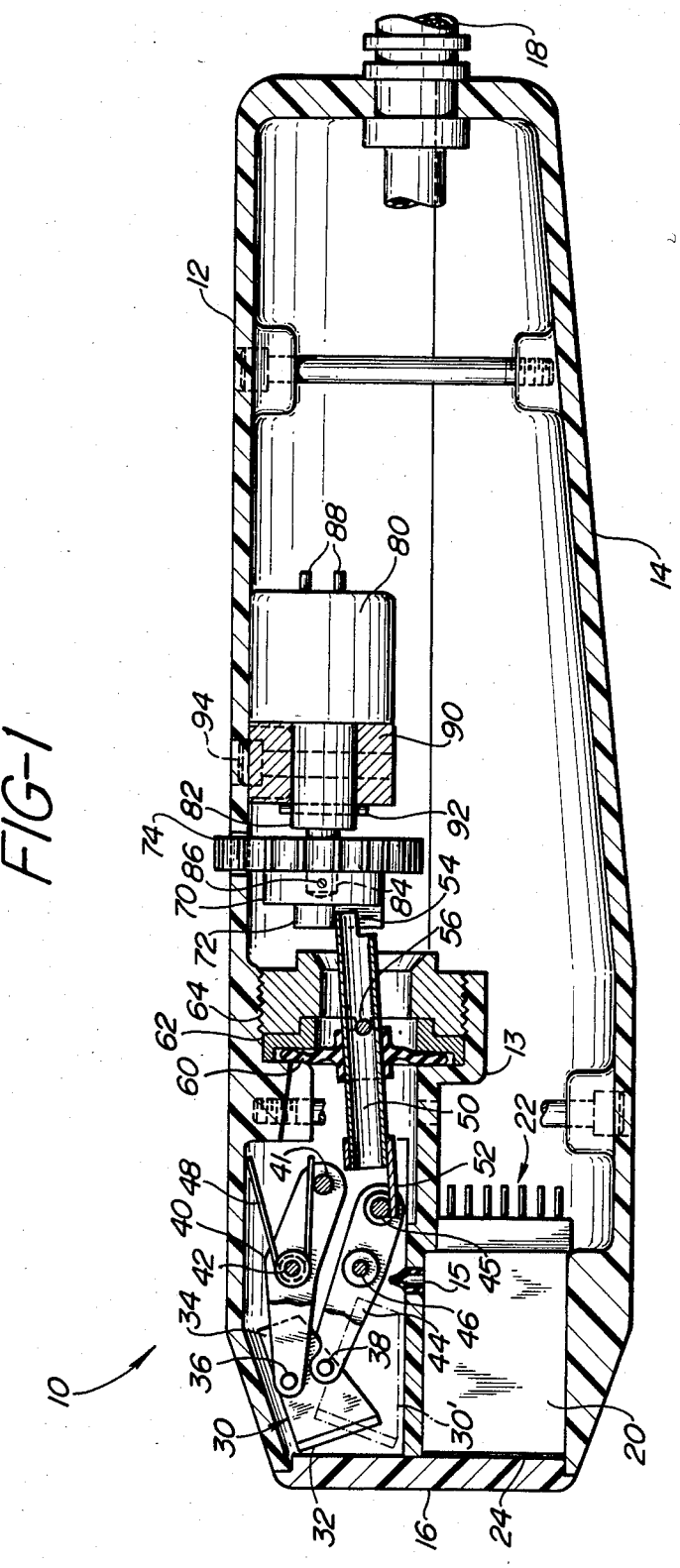

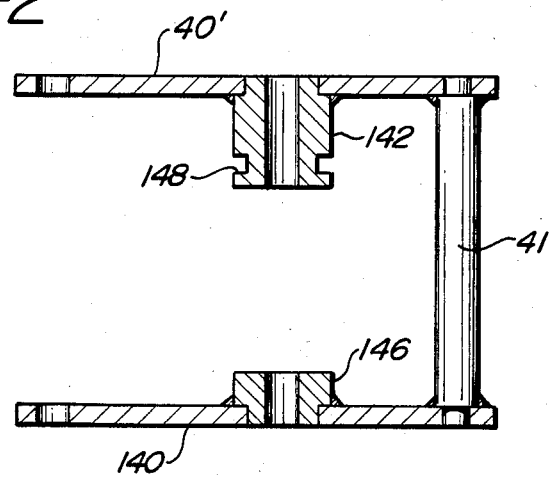
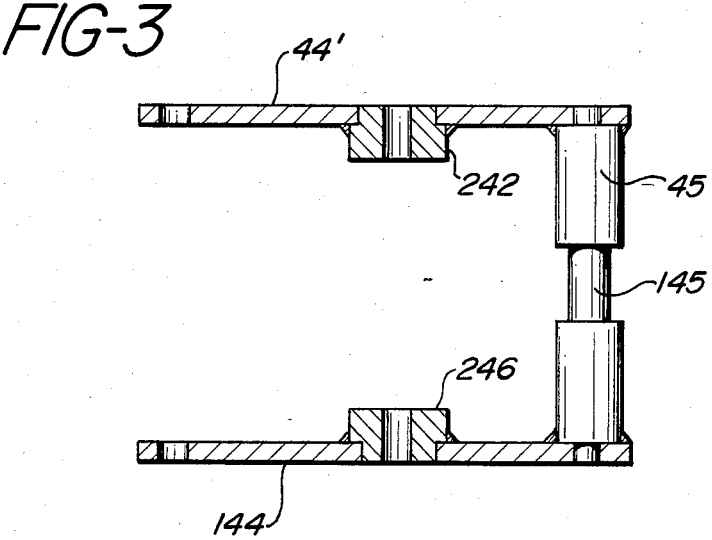

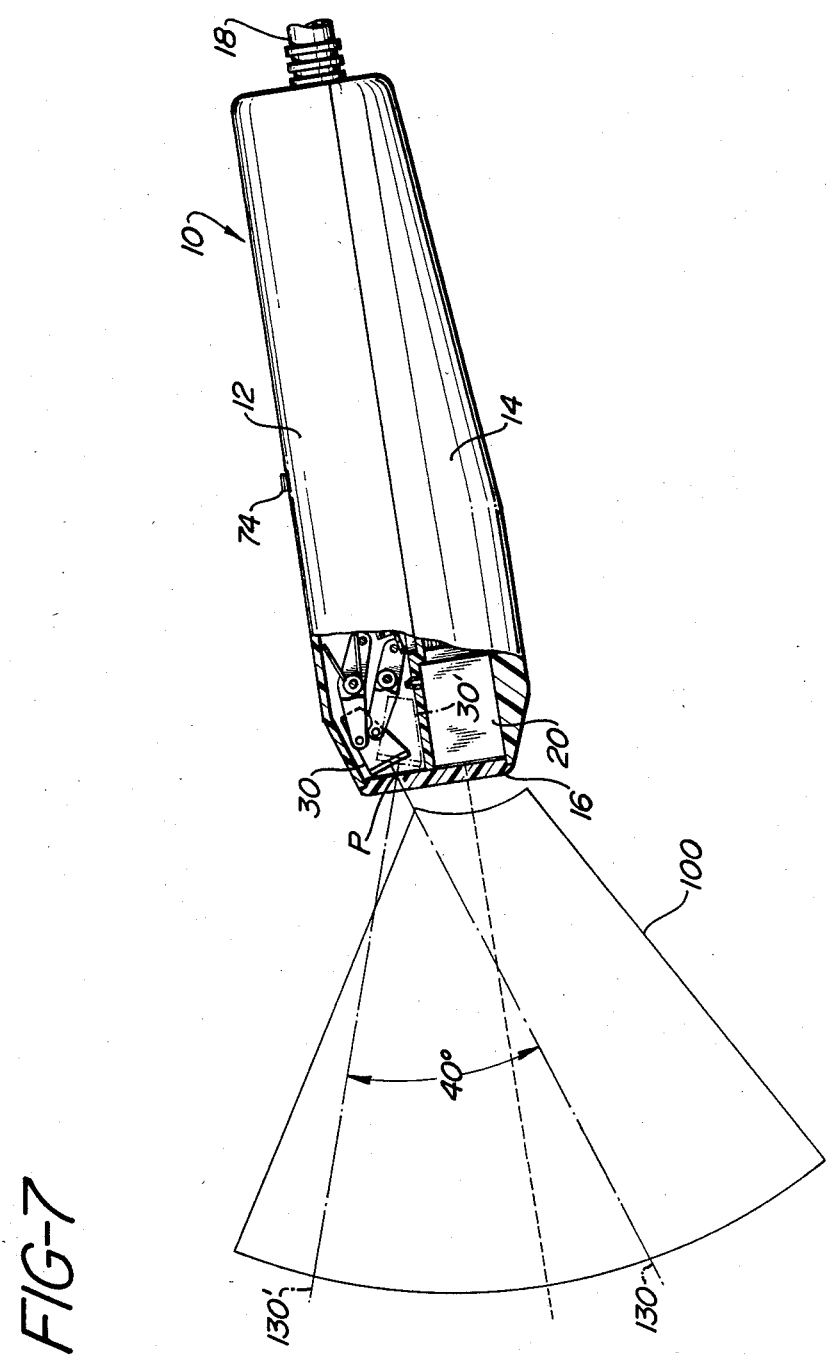

STEERABLE DOPPLER TRANSDUCER PROBES

This invention relates to ultrasonic transducer probes used for medical ultrasonic diagnosis and, in particular, to ultrasonic transducers used in the measurement of fluid flow which produce Doppler frequency-shifted signals.

In medical ultrasonic diagnosis, directed beams of ultrasound are used to noninvasively determine various characteristics of a patient's internal body structure and functions. For instance, ultrasonic waves can be repeatedly directed into the body in a pulse-echo format, with the time and direction of returning echoes providing an indication of the location of tissue interfaces. The echo information can thus be used to form a two-dimensional image of internal body structure.

Another use of medical ultrasound is to direct discrete pulses or a continuous beam of ultrasound toward a moving fluid in the body, such as moving blood in an artery, vein or chamber of the heart. The movement of the blood will cause the returning echo to exhibit a shift in frequency relative to the frequency of the transmitted beam due to the Doppler principle. A comparison of the transmitted and received frequencies will yield a measurement of the rate of flow of the blood.

Systems are known in the medical ultrasound art which perform pulse-echo imaging and others are known which perform Doppler flow measurement. It is desirable for a system which performs Doppler flow measurement to also be capable of performing simultaneous imaging. Without such a capability, the physician or sonographer cannot be certain of the exact location of the fluid being measured. This is particularly true when blood flow in the heart is being measured. Without an image indicating just where the Doppler beam is being directed, it is diffcult to be certain of just which chamber of the heart is being measured for its blood flow characteristics.

An ultrasonic transducer which addresses this need is shown and described in U.S. Pat. No. 4,492,120, entitled "DUAL FUNCTION ULTRASONIC TRANSDUCER ASSEMBLY". The hand-held assembly, or probe, which contains the transducers includes both a phased array imaging transducer and, adjacent to the imaging transducer, one Doppler transducer arrangement of two elements. While the phased array transducer is producing a two-dimensional image, one of the Doppler elements is directing a beam of ultrasound across the plane being imaged, and the other Doppler element is receiving the frequency-shifted Doppler signal when continuous wave Doppler measurements are being made. In the pulsed Doppler mode, the two elements are electrically connected together and alternately transmit and receive Doppler signals. While the operator is holding the probe against the patient's body, he or she is observing the image on a monitor. The image includes a cursor display which indicates the path of the Doppler beam. The operator can then move the probe along the patient's skin until the cursor is directed at the location where flow is to be measured, which can be found by watching the superimposed image of the internal body structure.

This technique of imaging and flow measurement is very useful when abdominal or peripheral vascular (carotid artery) regions are being examined. However, it presents limitations when blood flow in and around the heart is being measured. Ultrasonic energy does not reliably penetrate through bone, and the chest cavity is surrounded by the rib cage. It is therefore necessary to hold the probe so that the ultrasonic energy is directed to pass between the ribs. Once the probe is located in a favorable position, though, movement of the probe necessary to properly direct the Doppler beam to the desired location can cause one or the other of the Doppler and imaging beams to intercept a rib, making simultaneous imaging and flow measurement difficult or impossible. It would be desirable, once a favorable ultrasound aperture between the ribs is located, to be able to move the Doppler beam in various directions through the image plane without having to move the probe.

In accordance with the principles of the present invention, an ultrasonic diagnostic probe is provided which performs both imaging and Doppler flow measurement. The position of the Doppler transducer is adjustable by operation of a mechanical assembly, which permits the Doppler beam to be steered without moving the probe. The Doppler beam may be moved through an arc in the imaged region of the body by either a manual adjustment or actuation of a motor in the probe. Means are provided for indicating the various positions of the Doppler beam path in the two-dimensional image.

IN THE DRAWINGS

FIG. 1 illustrates in partial cross-sectional view an imaging and Doppler ultrasound probe constructed in accordance with the principles of the present invention;

FIGS. 2, 3, 4a, 4b, 5 and 6 illustrate in further detail some of the components of the mechanical assembly used to steer the Doppler transducer in the probe of FIG. 1; and FIG. 7 illustrates the principles of operation of the probe of FIG. 1.

Figure 4A:
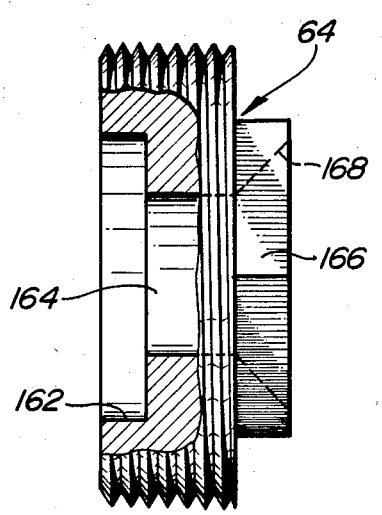

Referring to FIG. 1, an ultrasound probe constructed in accordance with the principles of the present invention is shown. The probe components are housed in a cast polyurethane case 10, including an upper case half 12 and a lower case half 14. An acoustic window 16 is fixed to the front of the case. In a constructed embodiment, the window is composed of two parts, one for the Doppler transducers and one for the imaging transducers. At the back of the case is a strain relief cable 18, through which electrical connections are made to components within the case.

At the front of the lower case half 14 and in contact with the acoustic window 16 is a phased array transducer assembly 20. The piezoelectric transducer elements are located on the front surface 24 of the assembly, and are acoustically coupled to the acoustic window 16 by an acoustic coupling medium such as epoxy. Behind the elements is a backing absorption layer through which wires from the elements extend to connect to pins 22 at the back of the assembly 20. The transducer assembly 20 is of the type described in detail in the aforementioned U.S. Pat. No. 4,492,120. Not shown in the FIGURE are the wires running from the pins 22 to the cable 18, which carry excitation signals to and echo signals from the imaging transducer assembly 20.

In the cavity of the upper case half 12 are the components of a steerable Doppler assembly constructed in accordance with the principles of the present invention. One or more Doppler transducers 32 are mounted on the face of a Doppler transducer assembly 30. When a continuous wave Doppler system is employed, two transducers will be used, one for transmission and one for reception. If only pulsed Doppler is employed, a single transducer may be used for alternate transmission and reception. Behind the transducers is a block 34 of backing material through which wires from the transducers extend and pass out the back of the block. Extending from either side of the block 34 are two pins 36 and 38 which are used to mount the transducer assembly in the mechanical linkage which moves the assembly. The upper pins 36 fit into holes of arms of a spring link 40. FIG. 2 illustrates another view of the spring link, showing both arms 40' and 140. At the end of the spring link remote from the transducer assembly the arms are connected by a rod 41. In the middle of the arms are hubs 142 and 146, which fit over axle pins 42, which extend from either side of the upper case half 12. The spring link 40 is thus mounted in FIG. 1 so as to pivot about the axle pins 42. A torsion spring 48 is mounted in a groove 148 of the hub 142. One end of the spring 48 presses upward against the top of the case, and the other end of the spring presses downward against the rod 41.

The lower pins 38 of the transducer assembly 30 are fitted into holes in the arms 44' and 144 of a drive link 44. The drive link is shown in another view in FIG. 3. In the middle of the drive link are two hubs 242 and 246, which fit over axle pins 46 in FIG. 1. This allows the drive link 44 to pivot about the axle pins 46, which extend from the sides of the upper case half 12 like the pins 42. FIG. 3 also shows the drive link arms connected by a rod 45. The rod 45 is machined in the middle to a smaller diameter as shown at 145.

A rocker tube 50 is mounted to pivot about a pivot pin 56. The pivot pin rides in a grove in a seal gland, as described below. A tongue 52 extends from the forward end of the rocker tube and presses against the smaller diameter portion 145 of the rod 45 of the drive link 44. At the other end, half of the rocker tube is cut away so that the remaining half cylinder 54 is in contact with a cam surface.

Because the Doppler transducers 32 are free to move about in the probe and are not in continual contact with the acoustic window 16, an acoustic coupling medium between the Doppler transducers and the acoustic window 16 must be provided. This is done by forming a fluid chamber about the Doppler transducers. The fluid chamber is formed by a portion of the upper case half 12, the acoustic window 16, a middle shell 13, and a seal 60. The middle shell 13 is fixed in place by a bead of silicone rubber, which runs about its perimeter. Located in the middle shell is a valve 15, which is a fill port through which fluid is injected into the sealed chamber. The rear portion of the middle shell together with the part of the upper case half above it forms a threaded opening for the seal 60 and its associated parts.

Figure 4B:
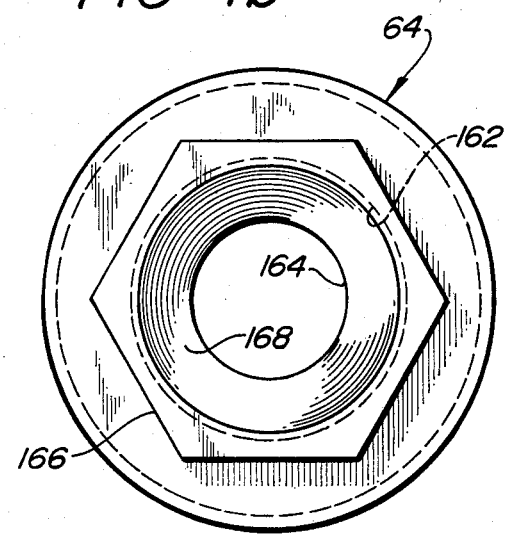
Figure 5:
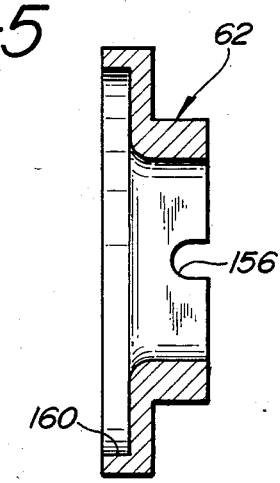

The disk-shaped seal 60 contains a flanged hole in the center which seals around the rocker tube 50. The seal 60 is pressed against the middle shell 13 and the upper case half 12 by a seal gland 62. The seal gland 62 is also shown in FIG. 5 and contains a larger diameter disk-shaped opening 160 which holds the seal 60 and presses it in a fluid-tight fit. The rocker tube passes through the hole in the center of the seal gland, and a grove 156 in the back of the seal gland holds the pivot pin 56. The seal gland is held in place in the space 162 of a gland nut 64, shown also in FIGS. 4a and 4b. The gland nut is threaded on its outermost surface and screws in place by turning the nut portion 166. The rocker tube 50 also passes through the gland nut through hole 164. The hole 168 through the nut portion 166 is flared to accommodate the range of movement of the rocker tube.

Figure 6:
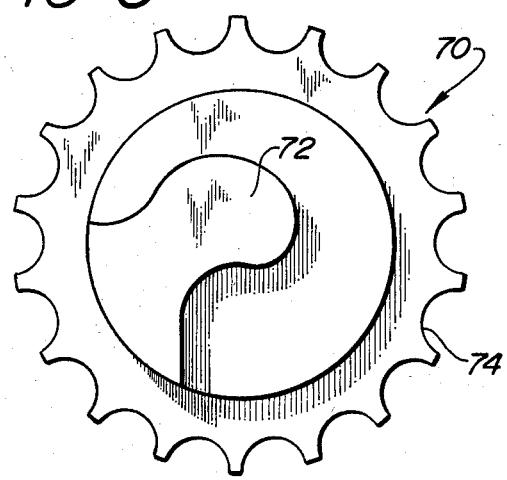

As mentioned above, the end 54 of the rocker tube contacts a cam surface. This cam surface 72 is formed in a cam thumbwheel 70. The cam thumbwheel 70, also shown in a plan view in FIG. 6, is mounted on the shaft 84 of a potentiometer 80, and is held in place by a set-screw 86. The threaded neck 84 of the potentiometer is located in a hole in a bracket 90 and a nut 92 screws onto the potentiometer neck to hold the potentiometer in the bracket 90. The bracket is held in place by screws located in two holes 94, shown in phantom in FIG. 1. At the back of the potentiometer are three terminals 88, two of which are shown in FIG. 1.

The spring 48 maintains the moving parts of the steerable Doppler mechanisms in contact with each other and eliminates backlash throughout the mechanisms. The spring pushes down on the rod 41, which pivots the spring link about the axle pins 42 and pulls the pin 36 and the Doppler transducer assembly upward. Pin 38 in turn exerts an upward force on the drive link 44, pivoting it about axle pins 46 and urging the rod 45 downward against the rocker tube tongue 52. This downward force rocks the rocker tube 50 about the pivot pin 56 and the end 54 of the rocker tube is urged upward in contact with the cam surface 72.

As the thumbwheel 74 is turned, the cam surface 72 rotates and pushes the end 54 of the rocker tube downward from the position shown in FIG. 1. The tongue end of the rocker tube pivots upward, lifting up against the rod 45. The drive link pivots about the axle pins 46 and pulls the transducer assembly 30 downward, thereby pivoting the spring link about the axle pins 42. The simultaneous pivoting of the drive and spring links not only moves the transducer assembly 30 downward, but also causes the transducer assembly to pivot about a point located in front of the Doppler transducers. When the transducer assembly is pivoted fully down, it is located as shown in phantom at 30'. The Doppler transducer assembly 30 thus pivots in a manner which requires an acoustic window for it which is only slightly larger than the face of the assembly on which the transducers are mounted. This allows the probe to be relatively small and hence easy to manipulate and use.

As the cam thumbwheel is turned, the shaft 84 of the potentiometer is also turned. The impedance of the potentiometer therefore represents the orientation of the Doppler transducers. Wires from the cable 18 are connected to the potentiometer terminals 88 to apply an energizing signal to the potentiometer so that its impedance may be measured. The wires from the Doppler transducers 32 are also connected to the cable. The Doppler transducer wires exit the fluid chamber by passing through the rocker tube 50, which is then potted with epoxy to seal the fluid chamber.

The operation of the imaging and Doppler transducer of the present invention is illustrated in FIG. 7. The imaging transducer 20 produces an image of the region described by the sector 100. When blood flow in a chamber of the heart is to be measured, for instance, the ultrasonic beams of sector 100 are directed through the ribs and the heart is imaged in sector 100. While the heart is being imaged and the probe is held in this position, the thumbwheel 74 is turned to steer the Doppler beam to the precise point where a measurement is to be taken. When the Doppler transducers are in the position shown at 30, the Doppler beam is directed as shown by line 130. As the thumbwheel 74 is turned the Doppler transducers move toward the position indicated at 30'. This sweeps the Doppler beam through an arc to the direction indicated by line 130'. In a constructed embodiment of the present invention, the arc is approximately 40°, and the effective point about which the Doppler beam pivots is located as shown by point P. The positional signals provided by the potentiometer are used to display a cursor in the sector image indicating the position of the Doppler beam as shown by lines 130 and 130' or any position therebetween.

It will be apparent that the potentiometer could be replaced by a motor and the thumbwheel dispensed with so that the Doppler transducer is steered remotely by a control on the ultrasound machine, for instance. If the motor is a stepping motor, for example, the directional energizing pulses applied to the motor to turn the motor shaft would be counted to continuously track the Doppler beam position and display the beam-representative cursor on the sector image display. It will also be apparent that other position feedback sensors may be used in place of the potentiometer, such as an optical encoder, for instance.

What is claimed is:

1. An ultrasonic diagnostic probe which is capable of performing ultrasonic imaging and Doppler measurement, comprising:
   a hollow case having an acoustic window which passes ultrasonic energy and including chamber means for containing fluid located within said hollow case and adjacent to a portion of said acoustic window;
   imaging transducer means, located in said hollow case and outside said fluid chamber means, and oriented to direct ultrasonic energy through said acoustic window toward an area which is to be imaged;
   Doppler transducer means, located in said hollow case within said fluid chamber means, and movably oriented to direct Doppler signals through said acoustic window toward said imaged area;
   means located within said fluid chamber means and externally controlled for controllably moving said Doppler transducer means to select one of a plurality of axes in said imaged area along which said Doppler signals are to be directed; and
   means, located external to said fluid chamber means and responsive to said means for moving, for providing an indication signal for identifying said selected axis.

2. The ultrasonic diagnostic probe of claim 1, wherein said means for controllably moving comprises a manually actuated mechanical assembly, located in said fluid chamber means and connected to said Doppler transducer means.

3. The ultrasonic diagnostic probe of claim 2, wherein said mechanical assembly includes means for pivoting said Doppler transducer means through an arc by pivoting said Doppler transducer means about a point located between said Doppler transducer means and said imaged area.

4. The ultrasonic diagnostic probe of claim 1, wherein said means for identifying includes a potentiometer.

5. The ultrasonic diagnostic probe of claim 4, wherein said moving means includes
   a motive member passing through a wall of said fluid chamber means and mechanically connected to said Doppler transducer means; and
   a cam, located within said hollow case and outside said fluid chamber means, and in contact with said motive member, wherein movement of said cam causes said Doppler transducer means to move in a controlled manner.

6. The ultrasonic diagnostic probe of claim 5, further comprising a thumbwheel, connected to said cam, for turning said cam.

7. The ultrasonic transducer probe of claim 5, wherein said moving means further includes:
   a pivoting arm, located within said fluid chamber means, and having a first end connected to said Doppler transducer means and a second end connected to said motive member,
   wherein movement of said motive member moves said Doppler transducer means by pivoting said arm about a pivot point.

8. The ultrasonic transducer probe of claim 7, wherein said moving means further includes:
   a second pivoting arm, located within said fluid chamber means, and having a first end connected to said Doppler transducer means and a second end,
   wherein said pivoting arms cooperate to permit said Doppler transducer to be moved through an arc centered about a point located between said Doppler transducer means and said imaged area.

9. The ultrasonic transducer probe of claim 8, wherein said moving means further includes a spring, in contact with said second end of said second pivoting arm, for spring-loading said moving means.

10. The ultrasonic transducer probe of claim 9, wherein said motive member comprises a tube, passing through a seal in said fluid chamber means wall, and pivotally mounted in the proximity of said wall.

11. An ultrasonic diagnostic probe which is capable of performing ultrasonic imaging and Doppler measurement, comprising:
    a hollow case;
    imaging transducer means, located in said case, for producing a two-dimensional image of a region being imaged;
    Doppler transducer means, located in chamber means for containing fluid within a portion of said case, for directing a beam of Doppler ultrasound toward said region being imaged;
    means for controllably moving said Doppler transducer to select one of a plurality of axes along which said beam of ultrasound is to be directed; and
    means, responsive to said controllably moving means, for developing an indication signal of the selected axis.
    wherein said imaging transducer means is located external to said fluid chamber means.

12. The ultrasonic diagnostic probe of claim 9, wherein said means for controllably moving comprises a mechanical assembly, connected to said Doppler transducer means, for mechanically adjusting the orientation of said Doppler transducer means toward said region being imaged; and
    wherein said indication signal developing means comprises variable impedance means, coupled to said mechanical assembly, for exhibiting an impedance which is representative of the orientation of said Doppler transducer means.

13. An ultrasonic diagnostic probe for ultrasonic imaging and Doppler flow measurement, comprising:
a hollow case
a fluid chamber located with a portion of said case;
imaging transducer means, located in said case external to said fluid chamber, for producing a two-dimensional image of a region of a patient's body;
Doppler transducer means, rotatably mounted within said fluid chamber, for controllably directing a Doppler ultrasound signal along one of a plurality of arcuately dispersed axes in said region being imaged; and
means, responsive to said Doppler transducer means, for producing an indication signal representative of the axis along which said Doppler ultrasound signal is directed.

* * * * *